United States Patent
Delnevo et al.

(10) Patent No.: US 7,115,107 B2
(45) Date of Patent: Oct. 3, 2006

(54) BLOOD CIRCUIT FOR A DIALYSIS MACHINE AND CORRESPONDING DIALYSIS MACHINE

(75) Inventors: Annalisa Delnevo, Correggio (IT); Carlo Alberto Lodi, Novi Di Modena (IT)

(73) Assignee: Gambro Lundia AB, Lund (SE)

( * ) Notice: Subject to any disclaimer, the term of this patent is extended or adjusted under 35 U.S.C. 154(b) by 421 days.

(21) Appl. No.: 10/343,856

(22) PCT Filed: May 30, 2002

(86) PCT No.: PCT/IB02/01953

§ 371 (c)(1),
(2), (4) Date: Feb. 5, 2003

(87) PCT Pub. No.: WO02/102440

PCT Pub. Date: Dec. 27, 2002

(65) Prior Publication Data

US 2003/0130607 A1   Jul. 10, 2003

(30) Foreign Application Priority Data

Jun. 15, 2001 (IT) .............................. TO01A0583

(51) Int. Cl.
- *A61M 37/00* (2006.01)
- *C02F 1/00* (2006.01)
- *C02F 1/37* (2006.01)
- *B01D 11/00* (2006.01)

(52) U.S. Cl. ................... 604/6.15; 604/4.01; 604/5.01; 210/646; 210/650; 210/746; 210/195.1; 210/257.1; 73/861.49

(58) Field of Classification Search ............... 604/4.01, 604/5.01–5.04, 6.09, 6.11, 6.15, 6.16, 262, 604/246, 403, 408–10; 141/69, DIG. 1; 417/437, 474–476, 477.1, 477.2, 477.9, 477.12; D24/107, 111, 112, 127–131; 210/600, 739, 210/644–646; 128/DIG. 24; 383/38–41, 383/105; 73/861.42, 861.47, 861.49, 861.51, 73/232, 262; 206/219, 221, 222, 828; 215/379–381; 220/500–1, 660, 666
See application file for complete search history.

(56) References Cited

U.S. PATENT DOCUMENTS 4,666,598 A    5/1987   Heath et al.
5,644,240 A *  7/1997   Brugger ..................... 324/439

FOREIGN PATENT DOCUMENTS

| EP | 0 766 947 A2 | 4/1997 |
| FR | 2 067 572 | 8/1971 |
| WO | WO 99/12588 | 3/1999 |
| WO | WO 99/24145 | 5/1999 |
| WO | WO 01/47581 | 7/2001 |

* cited by examiner

*Primary Examiner*—Patricia Bianco
(74) *Attorney, Agent, or Firm*—Finnegan, Henderson, Farabow, Garrett & Dunner, L.L.P.

(57) ABSTRACT

A blood circuit (1) for a dialysis machine is made form plastic material and is provided with a metallic plate (30), which is applied to an external face of the blood circuit (1) and is connectable to a voltage generator (34) in such a way as to form a capacitor, in which the plate (30) and the blood act as the capacitor plates and the plastic material acts as the dielectric.

16 Claims, 2 Drawing Sheets

BLOOD CIRCUIT FOR A DIALYSIS MACHINE AND CORRESPONDING DIALYSIS MACHINE

CROSS-REFERENCE TO RELATED APPLICATIONS

Figure 1:
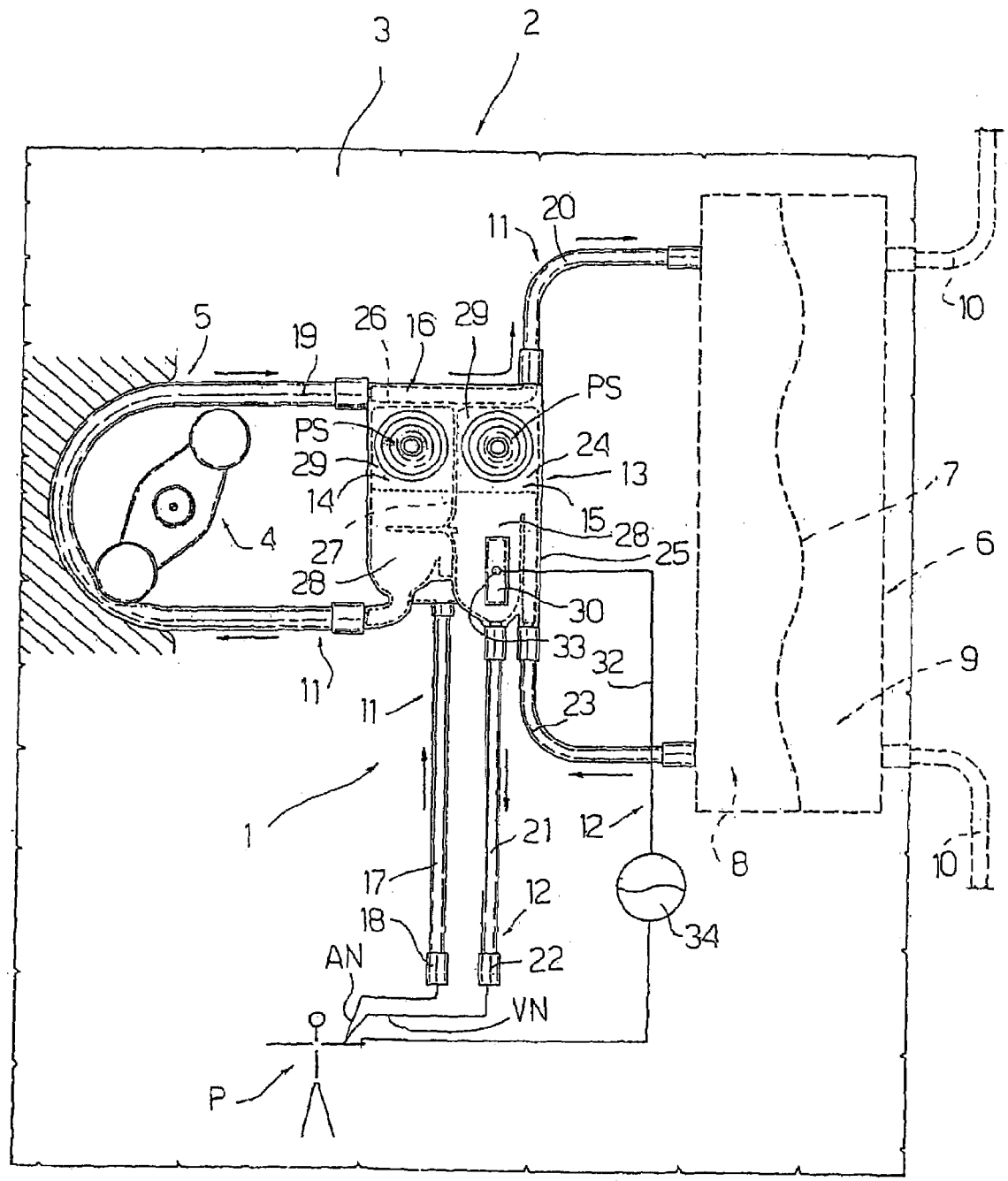

This application is an national phase application based on PCT/IB2002/01953, filed May 30, 2002, the content of which is incorporated herein by reference, and claims the right to priority based on Italian Application No. T02001A000583, filed Jun. 15, 2001.

BACKGROUND OF INVENTION

1. Field of the Invention

The present invention relates to a blood circuit for a dialysis machine.

As is known, blood consists of a liquid component, called the blood plasma, and a corpuscular component formed by the blood cells, including the red corpuscles among other types. In renal insufficiency, the blood contains, in addition to the aforesaid components, particles of low molecular weight (referred to below as the solute), which have to be eliminated by a dialysis treatment carried out by means of a dialysis machine.

A dialysis machine of a known type generally comprises a blood circuit, a dialysate circuit, and a filter which is connected to the aforesaid circuits and comprises a blood compartment and a dialysate compartment, which are separated from each other by a semi-permeable membrane, and through which pass, respectively, the blood to be treated and the dialysate, generally flowing in counter-current mode, when the machine is in operation.

During the dialysis treatment, the unwanted particles contained in the blood migrate from the blood compartment to the dialysate compartment both by diffusion and by convection, as a result of the passage of some of the liquid contained in the blood towards the dialysate compartment. The patient will therefore have lost some weight by the end of the dialysis process.

The blood circuit is connected to the patient by means of an arterial needle and a venous needle, which are inserted into a fistula formed in the patient's cardiovascular system, and are used, respectively, to collect the blood to be treated and to return the treated blood to the patient's cardiovascular system. The blood circuit comprises two expansion chambers (or droppers), one located in the arterial branch and one in the venous branch.

2. Background Art

In a known method for detecting the detachment of the venous needle from the patient and preventing blood loss due to the detachment of the venous needle, an electric current is injected into the blood circuit in such a way that the detachment of the venous needle is comparable to the opening of a circuit. Thus, by measuring the variation of electric current flowing in the blood circuit it is possible to detect the detachment of the venous needle.

For example, patent application WO 99/12588 describes a method in which the blood circuit is connected to an electrical circuit to inject a current into a closed circuit consisting of the blood circuit and the patient's cardiovascular system, and to measure, by means of a measuring instrument located in the aforesaid blood circuit, the variations of current caused by the detachment of one or both of the needles. In this method, the current injection and the measuring of the variation of current are carried out by means of inductive couplings located in the blood circuit, in other words by means of windings formed around the extracorporeal blood circuit at specified points of this circuit.

The placing of the windings around the blood circuit gives rise to problems of a practical nature, since the coupling between the blood circuit and the electrical circuit is laborious to set up and requires a certain amount of the operator's time.

BRIEF SUMMARY OF THE INVENTION

The object of the present invention is to provide a blood circuit which can be coupled in a simple and practical way to an electrical circuit.

According to the present invention, a blood circuit is provided for a dialysis machine, the blood circuit being made from plastic material and being characterized in that it comprises a metallic plate applied to an external face of the said blood circuit, the said plate being connectable to a voltage generator in such a way as to form a capacitor, in which the said plate and the blood act as the capacitor plates and the plastic material acts as the dielectric.

The advantages of the present invention are due to the replacement of the inductive coupling by a capacitive coupling, which can be formed simply by applying a metallic plate to the blood circuit at the point of the blood circuit where the electrical connection is to be made.

The present invention also relates to a dialysis machine for providing dialysis treatment to patients.

According to the present invention, a dialysis machine is made for carrying out dialysis treatments on patients, the machine comprising a blood circuit according to any one of the preceding claims, an electrical cable and the said voltage generator for supplying, when in use, an electric current through a preferential current-carrying circuit comprising the blood circuit, the electrical cable and a patient connected to the said blood circuit.

BRIEF DESCRIPTION OF THE SEVERAL VIEW OF THE DRAWINGS

Figure 2:
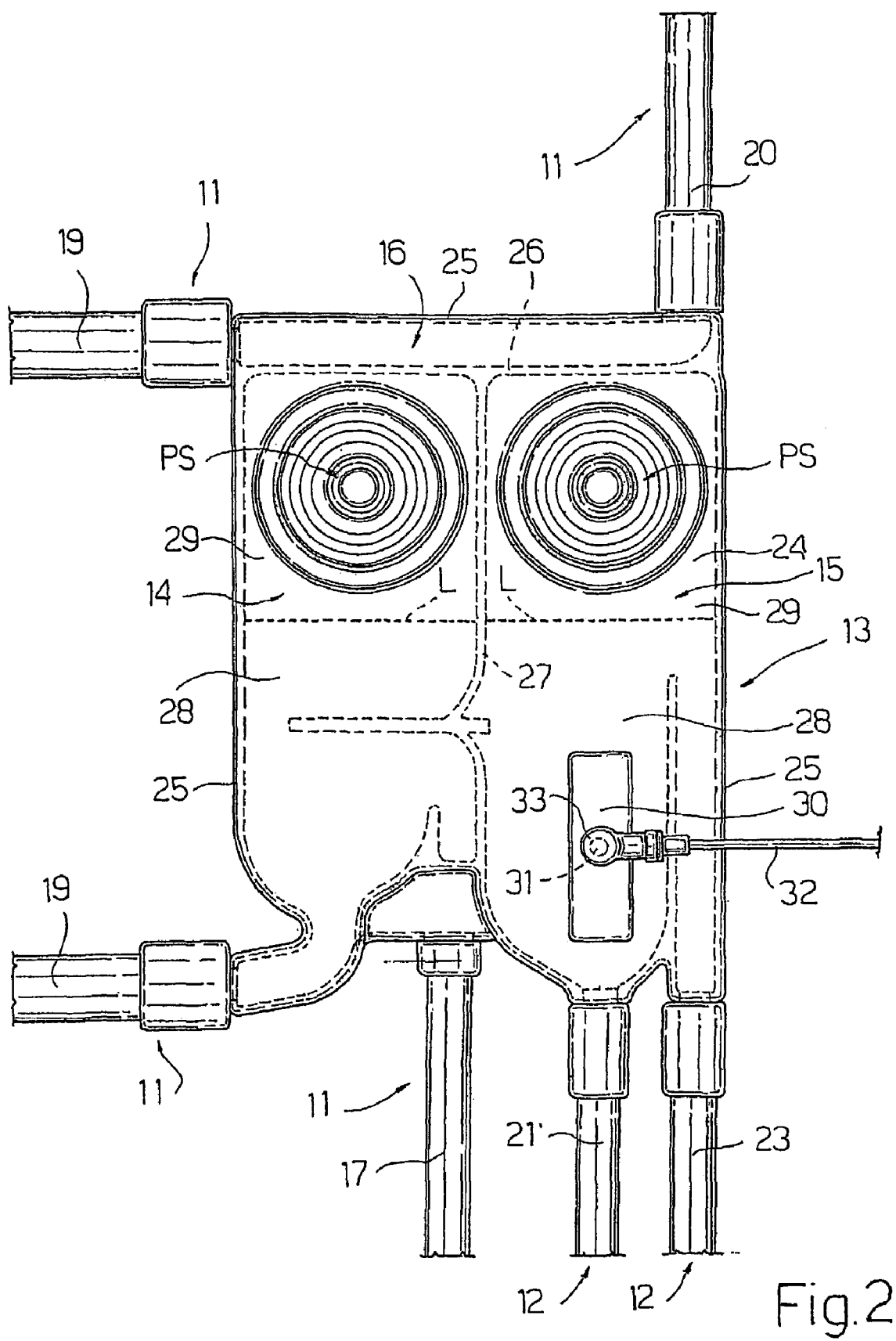

The present invention will now be described with reference to the attached drawings, which show a non-restrictive example of its embodiment, in which, FIG. 1 is a schematic view, with parts removed for clarity, of a blood circuit associated with a dialysis machine; and FIG. 2 is a view, on an enlarged scale, of a detail of the circuit of FIG. 1.

DETAILED DESCRIPTION OF THE INVENTION

In FIG. 1, the number 1 indicates the whole of a blood circuit for a dialysis machine 2.

The machine 2 is provided with a machine casing 3, which supports a rotor 4 which, in conjunction with a circuit 1, forms a peristaltic pump 5; a filter 6, which is shown in broken lines and comprises a semi-permeable membrane 7 which separates a blood compartment 8 from a dialysate compartment 9; and a dialysate circuit 10, which is shown in broken lines and is connected to the dialysate compartment 9 of the filter 6.

The circuit 1 has an arterial branch 11, a venous branch 12 and a box 13, which comprises an expansion chamber 14 in the arterial branch 11, an expansion chamber 15 in the venous branch 12, and a channel 16 located above the expansion chambers 14 and 15. The arterial branch 11 comprises a portion 17, which extends between the expansion chamber 14 and a connector 18 for connecting the arterial branch 11 to an arterial needle AN, a portion 19, which is bent into a U-shape around the rotor 4 to form the peristaltic pump 5, and whose ends are connected to the expansion chamber 14 and to the channel 16, and a portion 20 which connects the channel 17 to the blood compartment 8 of the filter 6. The venous branch 12 has a portion 21, which extends between the expansion 15 and a connector 22 for connecting the venous branch 12 to a venous needle VN, and a portion 23, which extends between the expansion chamber 15 and the blood compartment 8 of the filter 6.

In operation, the arterial needle AN and the venous needle VN are connected to a fistula of a patient P, in order, respectively, to collect the blood from the patient P and return it to him.

The box 13 is made from rigid transparent material, while the arterial branch 11 and the venous branch 12 are made from transparent flexible plastic material.

With reference to FIG. 2, the box 13 comprises two principal opposed walls 24 (only one of which is shown in the attached figures), a perimetric wall 25 located between the principal walls 24, a partition 26 for separating the channel 16 from the expansion chambers 14 and 15, and a partition 27 for separating the expansion chambers 14 and 15 from each other.

During dialysis treatment, the blood occupies lower portions 28 of the corresponding expansion chambers 14 and 15, while the upper portions 29 are occupied by air. In practice, the division of each of the chambers 14 and 15 into a lower portion 28 and an upper portion 29 is marked by the level L of the blood in each of the expansion chambers 14 and 15. During the dialysis treatment, the level L is kept essentially constant by means of known control devices which are associated with the dialysis machine 2 and are not illustrated.

Each chamber 14 and 15 has a corresponding pressure sensor PS located in the upper portion 29, while the expansion chamber 15 has a conductive element in the form of at least a metallic plate 30, which is fixed to the lower portion 28 of the box 13.

Note that the conductive element may alternatively be a plastic element having conductive properties, such as a plastic element embedding conductive particles and/or conductive fibres and/or conductive filaments. Suitable materials for the particles, fibres, filaments can be Alluminium or Carbon.

The plate 30 is a strip of metallic material, and has a face in direct contact with the external face of the wall 24 and a face which is opposite the preceding one and supports an electrical connector 31. The number 32 indicates an electrical cable provided with an electrical connector 33 which can be joined to the connector 31 to connect the plate 30 to a voltage generator 34. With reference to FIG. 1, the electrical cable 32 also connects the voltage generator 34 to the patient P.

During the dialysis treatment, the blood is directed along the arterial branch 11 and the venous branch 12 in the direction shown by the arrows in FIG. 1, and passes through the blood compartment 8 of the filter 6 and the expansion chambers 14 and 15 of the box 13. The blood accumulates in the lower portions 28 of the expansion chambers 14 and 15.

In order to detect the detachment of the venous needle VN, the cable 32 is connected to the plate 30 through the connectors 31 and 33, and is connected to the patient P and is supplied by the generator 34.

Since blood and the plate 30 are conductors of electric current, and the plastic material from which the box 13 is made is an insulating material, the presence of the plate 30 on the portion 28 of the expansion chamber 15 effectively forms a capacitor, in which the plate 30 and the blood are the opposing plates and the wall 24 is the dielectric.

The applicant has found that the connections shown in FIG. 1 between the cable 32, the patient P and the blood circuit 1 provide a preferential circuit for the flow of the electric current, comprising the cable 32, the patient P, the portion 21 of the venous branch 12 and the lower portion 28 of the expansion chamber 15.

Consequently, any discontinuity between the venous branch 12 and the patient P causes a significant variation of the current in the aforesaid preferential electrical circuit. This variation can be measured, for example, by measuring the variation of voltage across the terminals of an impedance located in the branch 32.

The detachment of the venous needle VN is therefore comparable to the opening of the aforesaid preferential electrical circuit, and is easily detectable by measuring the voltage.

The applicant has also found that the preferential electrical circuit does not differ from that described above when the end of the cable 32 connected to the patient P is connected to earth and the current flowing in the preferential circuit exceeds 10 kHz. In this case, the preferential electrical circuit is completed via the earth, regardless of whether the patient P is connected directly to earth or is not connected directly to earth. In the second case, the patient P in conjunction with the earth forms a capacitor, and, in electric terms, behaves in an essentially equivalent way to a patient P directly connected to earth when the frequency of the current flowing in the preferential circuit exceeds 10 kHz.

In a variant which is not shown, both of the expansion chambers 14 and 15 are provided with corresponding plates 30 for coupling both the arterial branch 11 and the venous branch 12 to the cable 32 by means of corresponding electrical connectors 33.

In a further variant which is not shown, the plate 30 can be located in any one of the portions of the venous branch 12 and the arterial branch 12, and can have an annular shape.

The present description implies that one or more plates 30 can be located at any point of the blood circuit 1 to electrically connect an electrical cable to the blood circuit 1 by means of a capacitive coupling.

The example which is described and illustrated is particularly advantageous, since it simplifies the electrical coupling between the electrical circuit and the blood circuit, while requiring only a single electrical connection.

The invention claimed is:

1. A blood circuit comprising:
   a first blood expansion chamber constructed of a plastic material, said first blood expansion chamber having a lower portion, configured to house blood when in use, and an upper portion configured to house air;
   a first pressure sensor located on said upper portion; and
   a first electrically conductive element fixed to an external face of said first blood expansion chamber in the area of said lower portion.

2. The circuit of claim 1, further comprising an arterial branch and a venous branch, said first blood expansion chamber being located in said venous branch.

3. The circuit of claim 2, further comprising:
a second blood expansion chamber located in said arterial branch, said second blood expansion chamber constructed of a plastic material, said second blood expansion chamber having a lower portion, configured to house blood when in use, and an upper portion configured to house air; and
a second pressure sensor located on said upper portion of said second blood expansion chamber.

4. The circuit of claim 3, comprising a second electrically conductive element applied to an external face of said second blood expansion chamber in the area of said lower portion.

5. The circuit of claim 4, wherein said second electrically conductive element comprises plastics embedding electrically conductive bodies.

6. The circuit of claim 5, wherein said electrically conductive bodies comprise fibers, and/or particles, and/or filaments.

7. The circuit of claim 4, wherein said second electrically conductive element comprises a metallic plate.

8. The circuit of claim 4, wherein said first blood expansion chamber and said second blood expansion chamber are integrated in a box made of rigid plastic material; said box comprising a first principal wall, a second principal wall, and a perimetric wall; said first pressure sensor, said second pressure sensor, said first electrically conductive element, and said second electrically conductive element being located on an external face of the first principal wall or the second principal wall.

9. The circuit of claim 3, wherein said first blood expansion chamber and said second blood expansion chamber are integrated in a box made of rigid plastic material.

10. The circuit of claim 1, wherein said first electrically conductive element is connectable to a voltage generator forming a capacitor, said first electrically conductive element and blood housed in said lower portion serve as capacitor plates and said plastic material of said first blood expansion chamber serves as a dielectric.

11. The circuit of claim 10, wherein said first electrically conductive element comprises a first electrical connector configured to be coupled to a second electrical connector of said voltage generator.

12. A dialysis machine comprising a blood circuit according to claim 10, and a voltage generator connected to said first electrically conductive element for supplying an electrical current through an electrical circuit comprising said blood circuit, wherein said blood circuit is connected to a patient.

13. The circuit of claim 1, wherein said first electrically conductive element comprises plastics embedding electrically conductive bodies.

14. The circuit of claim 13, wherein said electrically conductive bodies comprise fibers, and/or particles, and/or filaments.

15. The circuit of claim 1, wherein said first pressure sensor is located on said external face of said first blood expansion chamber.

16. The circuit of claim 1, wherein said first electrically conductive element comprises a metallic plate.

* * * * *

UNITED STATES PATENT AND TRADEMARK OFFICE
CERTIFICATE OF CORRECTION

PATENT NO. : 7,115,107 B2 Page 1 of 1
APPLICATION NO. : 10/343856
DATED : October 3, 2006
INVENTOR(S) : Annalisa Delnevo and Carlo Alberto Lodi It is certified that error appears in the above-identified patent and that said Letters Patent is hereby corrected as shown below:

On the title page, item (57), line 1, "form" should read --from--.

Signed and Sealed this

Fifth Day of December, 2006

JON W. DUDAS
*Director of the United States Patent and Trademark Office*